United States Patent
Chapuis et al.

(10) Patent No.: US 11,097,131 B2
(45) Date of Patent: Aug. 24, 2021

(54) EYE PROBE FOR TREATMENT WITH ULTRASONIC WAVES

(71) Applicant: EYE TECH CARE, Rillieux-la-Pape (FR)

(72) Inventors: Phillipe Chapuis, Pommiers (FR); Thomas Charrel, Mionnay (FR); Cedric Devigne, Villars les Dombes (FR); Nicolas Laisney, Villeurbanne (FR); Arash Razavi Mashoof, Lyons (FR)

(73) Assignee: EYE TECH CARE, Rilliex-la-Pape (FR)

(*) Notice: Subject to any disclaimer, the term of this patent is extended or adjusted under 35 U.S.C. 154(b) by 605 days.

(21) Appl. No.: 15/562,612

(22) PCT Filed: Mar. 30, 2016

(86) PCT No.: PCT/EP2016/056898
§ 371 (c)(1),
(2) Date: Sep. 28, 2017

(87) PCT Pub. No.: WO2016/156381
PCT Pub. Date: Oct. 6, 2016

(65) Prior Publication Data
US 2018/0111008 A1    Apr. 26, 2018

(30) Foreign Application Priority Data
Mar. 31, 2015    (FR) ..................... 15/00644

(51) Int. Cl.
*A61N 7/00*    (2006.01)
*A61F 9/007*    (2006.01)
(Continued)

(52) U.S. Cl.
CPC ............ *A61N 7/00* (2013.01); *A61F 9/007* (2013.01); *A61B 2017/2253* (2013.01);
(Continued)

(58) Field of Classification Search
None
See application file for complete search history.

(56) References Cited

U.S. PATENT DOCUMENTS 4,484,569 A * 11/1984 Driller .................. A61B 8/10
                                                          600/439
4,634,418 A    1/1987 Binder
(Continued)

FOREIGN PATENT DOCUMENTS

DE    20221042    12/2004
EP    0627202    12/1994
(Continued)

OTHER PUBLICATIONS

Rouland et al., "Étude observationnelle rétrospective de coûts des deux premiéres années de traitement dans le glaucome primitif à angle ouvert et l'hypertension oculaire en France", J Fr. Ophtalmol., 2001; vol. 24, No. 3, pp. 233-243.
(Continued)

*Primary Examiner* — Bill Thomson
*Assistant Examiner* — Younhee Choi
(74) *Attorney, Agent, or Firm* — Womble Bond Dickinson (US) LLP

(57) ABSTRACT

A probe for treating an ocular pathology. The probe has a ring including a cone frustum having a first end suitable for supporting an ultrasound generator and a second end for coming into contact with an eye of a patient. The ultrasound generator includes a first base intended to come to face the first end, and a second base opposite the first base. The probe further includes a flow regulator for eliminating the bubbles
(Continued)

Figure 3:
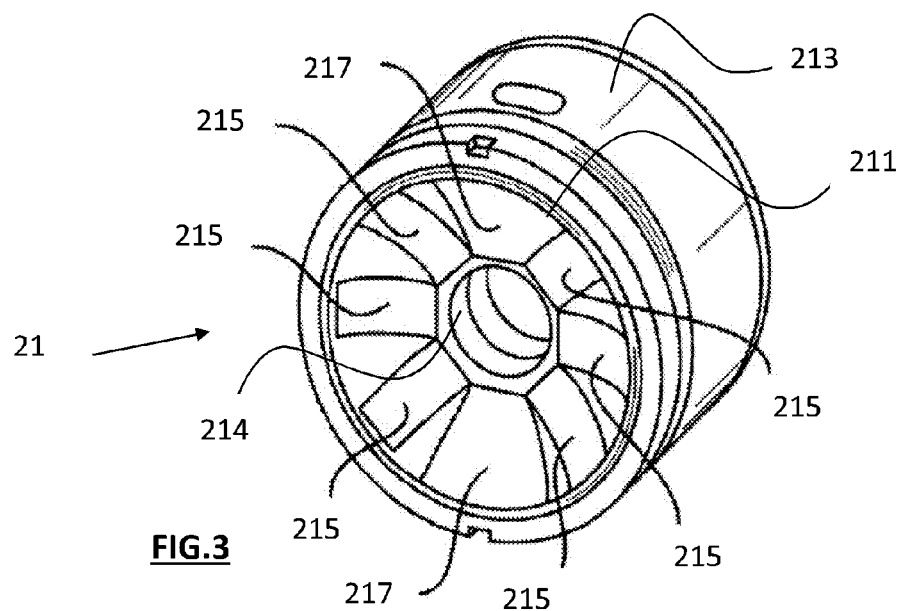

contained in a coupling fluid flowing to the first base when filling the probe with the fluid.

14 Claims, 2 Drawing Sheets

(51) Int. Cl.
 *A61B 17/225* (2006.01)
 *A61B 18/00* (2006.01)
(52) U.S. Cl.
 CPC . *A61B 2018/00291* (2013.01); *A61F 9/00781* (2013.01); *A61N 2007/0021* (2013.01)

(56) References Cited

U.S. PATENT DOCUMENTS

| | | | |
|---|---|---|---|
| 4,787,885 A | 11/1988 | Binder | |
| 4,936,825 A | 6/1990 | Ungerleider | |
| 4,946,436 A | 8/1990 | Smith | |
| 5,127,901 A | 7/1992 | Odrich | |
| 5,180,362 A | 1/1993 | Worst | |
| 5,230,334 A | 7/1993 | Klopotek | |
| 5,360,399 A | 11/1994 | Stegmann | |
| 5,433,701 A | 7/1995 | Rubinstein | |
| 6,039,689 A | 3/2000 | Lizzi | |
| 6,162,193 A * | 12/2000 | Ekberg | A61F 9/00745 604/22 |
| 6,267,752 B1 | 7/2001 | Svetliza | |
| 7,909,781 B2 * | 3/2011 | Schwartz | A61F 9/00781 601/2 |
| 8,043,235 B2 * | 10/2011 | Schwartz | A61F 9/00781 601/2 |
| 8,970,090 B2 * | 3/2015 | Akiyama | B06B 3/00 310/322 |
| 9,125,722 B2 * | 9/2015 | Schwartz | A61F 9/00781 |
| 2003/0116014 A1 * | 6/2003 | Possanza | B01D 19/0078 95/30 |
| 2003/0230690 A1 * | 12/2003 | Ostrovsky | F01D 15/10 248/316.7 |
| 2004/0015140 A1 | 1/2004 | Shields | |
| 2006/0209135 A1 * | 9/2006 | Hoisington | B41J 2/055 347/68 |
| 2012/0277597 A1 * | 11/2012 | Eshbaugh | A61B 5/684 600/481 |
| 2013/0023768 A1 * | 1/2013 | Hooriani | A61B 8/10 600/459 |
| 2013/0197633 A1 * | 8/2013 | Romano | A61F 2/14 623/4.1 |

FOREIGN PATENT DOCUMENTS

| | | |
|---|---|---|
| EP | 0627207 A1 | 12/1994 |
| EP | 1243236 A1 | 9/2002 |
| EP | 1306068 A2 | 5/2003 |
| EP | 1325722 A2 | 7/2003 |
| EP | 1350492 A2 | 10/2003 |
| EP | 1738725 A1 | 1/2007 |
| RU | 2200522 C1 | 3/2003 |
| RU | 2197926 C2 | 2/2010 |
| WO | 96/14019 A1 | 5/1996 |
| WO | 96/28213 A1 | 9/1996 |
| WO | 02/38078 A2 | 5/2002 |
| WO | 2006/018686 A1 | 2/2006 |
| WO | 2006/129047 A2 | 12/2006 |
| WO | 2006/136912 A1 | 12/2006 |
| WO | 2007/081750 A2 | 7/2007 |
| WO | 2008/024795 A2 | 2/2008 |
| WO | 2009/103721 A1 | 8/2009 |

OTHER PUBLICATIONS

Müller M., "Focusing water shock waves for lithotripsy by various ellipsoid reflectors", Biomed Tech (Berl), Apr. 1989, vol. 34, No. 4, pp. 62-72.
Lizzi et al., "Ultrasonic Theraphy and Imaging in Ophthalmology", 1985, XP002079832, pp. 1-17.
Lachkar et al., "Dépistage du glaucome chronique á angle ouvert", Encyclopédie Médico-Chirurgicale 21-275-A-20.
International Search Report and Written Opinion received for PCT Patent Application No. PCT/EP2016/056898, dated May 3, 2016, 16 pages.
International Preliminary Report on Patentability received for PCT Patent Application No. PCT/EP2016/056898, dated Oct. 12, 2017, 14 pages.
Hamard et al., "Traitement des glaucomes refractaires", Encycl Med Chir (Elsevier, Paris), Ophtalmologie, 21-280-8-50,1997, 8 pages.
Dépistage Et Diagnostic Précoce Du Glaucome : Problématique Et Perspectives En France, Haute Autorité de santé-Service évaluation médico-économique et santé publique Nov. 2006.
Coleman et al., "Therapeutic Ultrasound in the Treatment of Glaucoma", Ophthalmology, Mar. 1985, vol. 92, No. 3, pp. 339-346.
Chavrier et al., "Modeling of high-intensity focused ultrasound-induced lesions in the presence of cavitation bubbles", J. Acoust. Soc. Am., vol. 108, No. 1, Jul. 2000, pp. 432-440.
Bron et al., "Prevalence de l'hypertonie oculaire et du glaucome dans une population francaise non selectionnee", J Fr. Ophtalmol., vol. 29, No. 6, 2006, pp. 635-641.

* cited by examiner

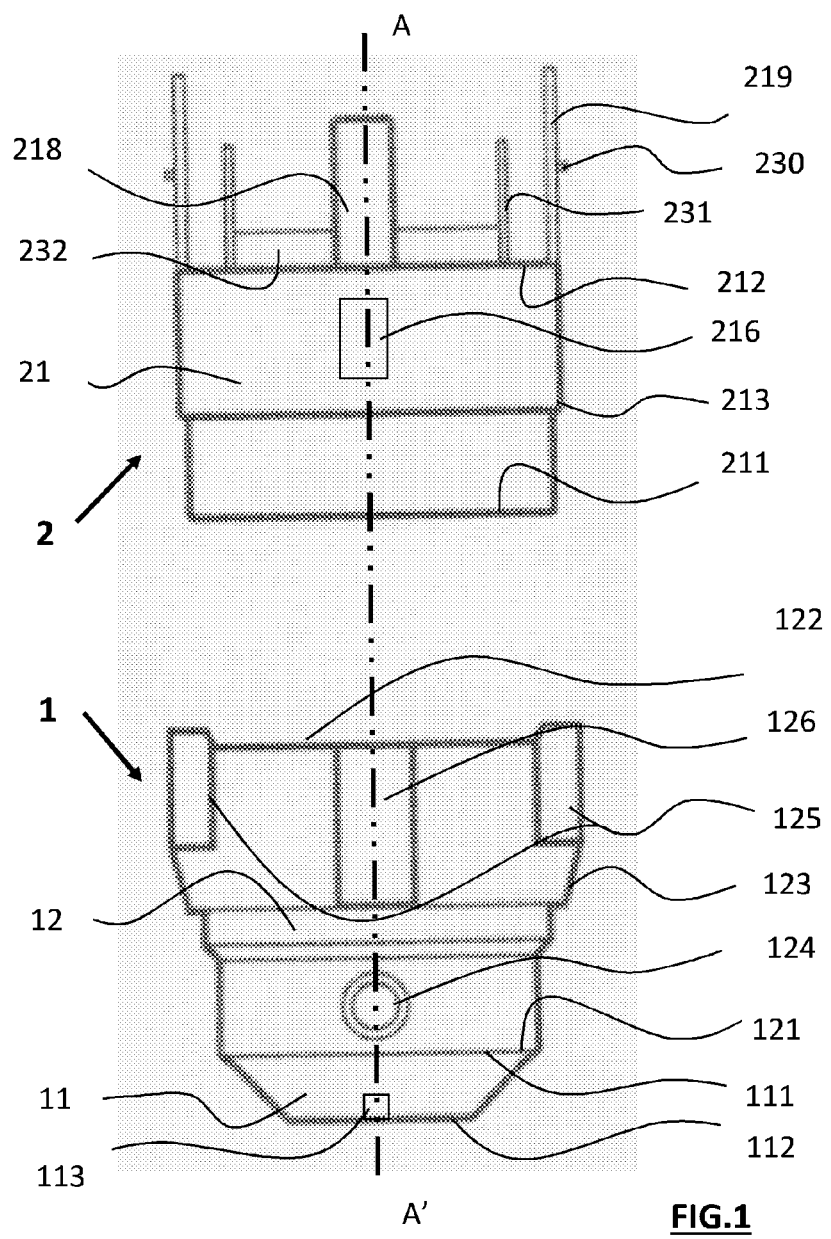
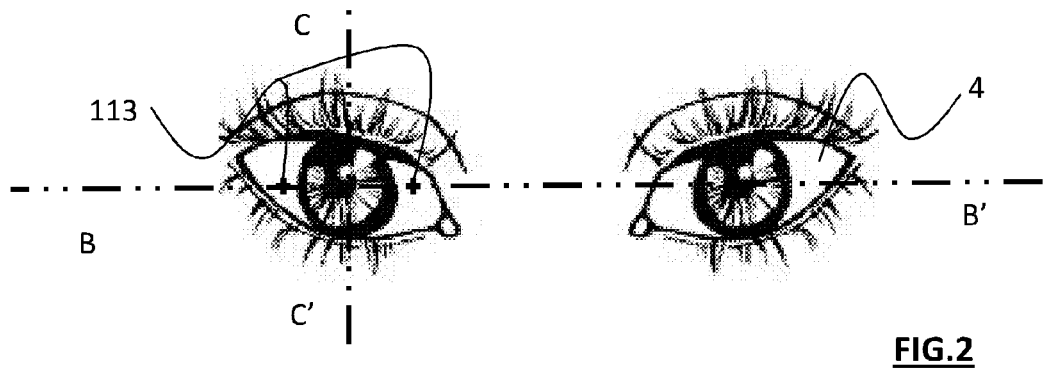

EYE PROBE FOR TREATMENT WITH ULTRASONIC WAVES

FIELD OF THE INVENTION

The present invention relates to the general technical field of non-invasive treatment devices for an eye pathology by generation of focused or non-focused ultrasonic waves, of high or low intensity.

More particularly, the invention relates to a probe of a device for generating ultrasonic waves for treating an eye pathology, such as for example the treatment of a glaucoma.

BACKGROUND OF THE INVENTION

Glaucoma is an optical neuropathy, i.e. a degeneration of the optical nerve, this leading very often to an increase in the intraocular pressure (IOP).

When the aqueous humor is no longer discharged sufficiently rapidly, the latter accumulates, which induces an increase in the IOP. The increase in the IOP compresses the axones in the optical nerve and may also compromise the vascularization of the optical nerve. A high IOP for a long period may induce a total loss of vision.

The only therapeutic approach presently available for treating glaucoma consists of reducing the intraocular pressure:
 either by improving the draining of the aqueous humor through the trabeculum and the Schlemm channel of the eye,
 or by reducing the production of aqueous humor by the ciliary body of the eye.

From document WO 2009/103721 a device is known for reducing the production of aqueous humor based on the principle of cyclo-coagulation with focused ultrasonic waves of high intensity which consists of destroying a portion of the ciliary bodies in order to reduce the production of aqueous humor.

The device described in WO 2009/103721 allows the treatment of one or several sectors of the eye in one single act. This device comprises a probe consisting of a ring and of means for generating ultrasonic waves.

The ring has a proximal portion intended to be in contact with an eye of a patient, and a distal portion intended to receive the means for generating ultrasonic waves.

The means for generating ultrasonic waves has a concave profile. More specifically, the means for generating ultrasonic waves comprise six transducers with the form of a cylinder segment positioned on a cylindrical crown of axis A-A'.

In order to allow transmission of the ultrasonic waves towards the eye of the patient, the six transducers have to be immersed in a coupling liquid. The coupling liquid is generally conditioned in a flask of the dropwise type consisting:
 of a container containing the coupling liquid,
 of a drop dispenser mounted on the container, and
 of a plug for closing the dispenser.

Once the ring is positioned on the eye to be treated, the practitioner is therefore forced to fill the ring with coupling liquid by applying pressure on the container for expelling the coupling liquid through the dispenser.

In order to limit the period of the filling step, the practitioner generally applies a very strong pressure so that the liquid is expelled in the ring as a jet.

During the gradual filling of the ring, this jet induces turbulences with the liquid already contained in the ring, which causes the formation of air bubbles which may come and be accommodated between the eye and the means for generating ultrasonic waves.

As air is not very permeable to ultrasonic waves, the presence of an air bubble between the eye and the means for generating ultrasonic waves may be detrimental to the efficiency of the treatment.

An object of the present invention is to propose a solution to the problem described above.

SHORT DESCRIPTION OF THE INVENTION

For this purpose, the invention proposes a probe for treating an eye pathology comprising:
 a ring including a truncated cone having a first end adapted for supporting means for generating ultrasonic waves and a second end for coming into contact with an eye of a patient,
 means for generating ultrasonic waves including a first base intended to come to face the first end, and a second base opposed to the first base,
remarkable in that the probe further comprises a flow rate regulator for suppressing the bubbles contained in a coupling fluid flowing towards the first base during the filling of the probe with said fluid.

Thus, the probe according to the invention comprises a flow rate regulator between the second and first bases of the generation means. This flow rate regulator includes a conduit for supplying a coupling fluid for which the dimensions are adapted for preventing the propagation towards the first base, of the bubbles contained in the coupling fluid.

Advantageously, the dimensions of the fluid supply conduit are calculated so as to limit the risks of propagation of bubbles when the coupling fluid has a viscosity equal to that of water. This gives the possibility of guaranteeing that the function of suppressing the bubbles of the regulator are effective for any coupling fluid having a viscosity greater than or equal to that of water.

As indicated earlier, the air bubbles are detrimental to the propagation of the ultrasonic waves because of their strong acoustic resistance.

The flow rate regulator gives the possibility of reducing the risk of presence of these air bubbles between the eye of the patient and the means for generating ultrasonic waves, which guarantees the whole efficiency of the probe.

Preferred aspects but non-limiting aspects of the treatment probe according to the invention are the following:
 the ring may comprise a coaxial skirt with the truncated cone, and the means for generating ultrasonic waves may comprise a crown, the skirt extending outwards from the first end so as to surround the crown;
 the regulator may comprise an aperture defined between the skirt and the crown, said aperture extending over the whole height of the crown for allowing passing of the fluid between the second and first bases;
 the aperture may extend over the whole perimeter of the crown;
 the thickness of the aperture may be comprised between 0.1 mm and 5 mm, preferentially between 0.2 and 2 mm, and still more preferentially equal to 0.5 mm;
 the first base of the means for generating ultrasonic waves may comprise a hydrophilic treatment;
 the probe may also comprise a purger for the exhaust of the gases during the filling of the probe with the coupling fluid;
 the means for generating ultrasonic waves may comprise a crown having a central channel, the purger comprising at least one chimney coaxial with the central channel and extending outwards on the second base;

the ring and the means for generating ultrasonic waves may be made in two distinct parts intended to be assembled, the probe comprising a guide for guiding the sliding of the means for generating ultrasonic waves relatively to the ring;

the guide may consist in a groove laid out on the ring and a slider laid out on the means for generating ultrasonic waves;

the probe may further comprise at least two suction nozzles on the second end, the nozzles being laid out so as to be localized in a temporal/nasal plane B-B' of the eye when the probe is positioned on the eye;

the means for generating ultrasonic waves may comprise a gripper extending on the second base;

the ring and the means for generating ultrasonic waves may be made in two distinct parts intended to be assembled, the probe comprising blockers for immobilizing the ring relatively to the means for generating ultrasonic waves;

the blockers may comprise a pair of elastic tabs with shape memory extending at the periphery of the second base, each tab including a bulge for cooperating by clipping with a bulge made on the ring so as to immobilize in translation the ring relatively to the means for generating ultrasonic waves;

each bulge may have a V shape;

the probe may further comprise at least one abutment for limiting the displacement of the tabs.

SHORT DESCRIPTION OF THE DRAWINGS

Figure 4:
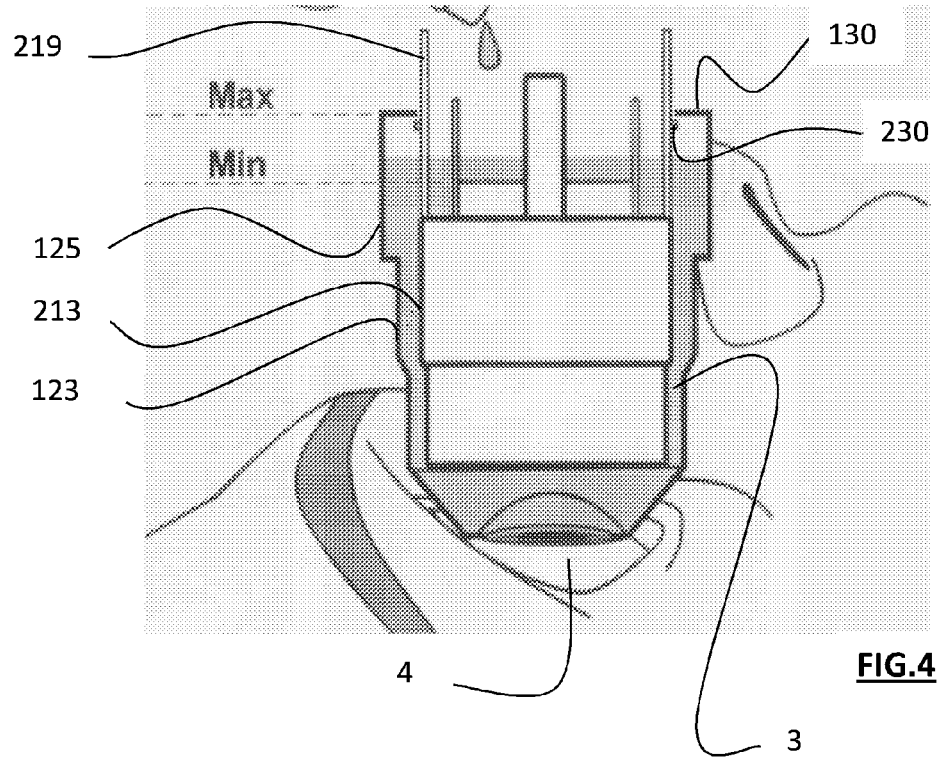

Other advantages and characteristics of the probe according to the invention will become better apparent from the description which follows of several alternative embodiments, given as non-limiting examples, from appended drawings wherein:

FIG. 1 schematically illustrates a ring and means for generating ultrasonic waves of the probe, FIG. 2 schematically illustrates the eyes of a patient, FIG. 3 is a perspective view of the means for generating ultrasonic waves, FIG. 4 schematically illustrates the probe once the ring and the means for generating ultrasonic waves are assembled.

DETAILED DESCRIPTION OF THE INVENTION

Different examples of the probe according to the invention will now be described with reference to the figures. In these different figures, equivalent elements are designated by the same numerical reference.

With reference to FIGS. 1 to 4, an embodiment is illustrated of the probe for treating an eye pathology.

The probe comprises:
a ring 1,
means for generating ultrasonic waves 2.

The means for generating ultrasonic waves 2 are intended to cooperate with the ring 1. More specifically, the ring 1 forms a housing for the means for generating ultrasonic waves 2.

1. Presentation of the Probe 1.1. Means for Generating Ultrasonic Waves

The means for generating ultrasonic waves 2 give the possibility of generating ultrasonic energy. For example, the means for generating ultrasonic waves give the possibility of generating focused ultrasonic waves with high intensity.

They comprise a ring-shaped crown 21 with an axis A-A' including:
first and second opposed bases 211, 212 orthogonal to the A-A' axis,
an external side wall 213 between the first and second bases, and
an internal side wall 214 defining a central channel between the first and second bases 211, 212.

The first base 211 include at least one transducer 215 having a radiating element for generating ultrasonic waves.

The profile of the radiating element(s) may be adapted for allowing the orientation and the focusing of the ultrasonic waves in a given point. Alternatively, the transducer 215 may comprise reflector(s) for reflecting, orienting and focusing in a given point the ultrasonic waves generated by the radiating element(s).

In the embodiment illustrated in FIG. 3, six transducers 215 extend over the first base 211 of the crown 21.

The transducers 215 are grouped in two pairs of three transducers separated by two inactive sectors 217.

The inactive sectors 217 are localized on the crown 21 so as to extend in a temporal/nasal plane B-B' of the eye 4 when the probe is set into place on the eye 4, these sectors 217 corresponding to areas of the eye 4 including the majority of the nerve and vascular endings.

1.2. Ring

The ring 1 allows adequate and constant positioning of the means for generating ultrasonic waves 2, both for the centering and for the distance relatively to the sclera of the means for generating ultrasonic waves 2.

The ring 1 comprises a truncated cone (or cone frustum) 11 with an axis A-A', and a peripheral skirt 12 coaxial with the truncated cone 11.

The truncated cone 11 is opened at both of its ends. The large base 111 of the truncated cone 11—a so called "first end" in the following—comprises a supporting cradle intended to receive the means for generating ultrasonic waves 2. The small base 112 of the truncated cone 11—a so called "second end" subsequently—is intended to come into contact with the eye 4. The second end 112 may comprise an external annular flange able to be applied on the external surface of the eye 4, this flange having a concave profile with a radius of curvature substantially equal to the radius of curvature of the eye 4.

The skirt 12 comprises a ring-shaped wall 123 coaxial with the truncated cone 11. The skirt 12 extends outwards from the first end 111 of the truncated cone 11. More specifically, the skirt 12 comprises first and second open endings 121, 122:
the first ending 121 being secured to the first end 111, and
the second ending 122 being opposed to the second end 112.

Advantageously, the skirt 12 has a shape mating the means for generating ultrasonic waves 2. More specifically, the interior profile of the ring-shaped wall 123 is the conjugate of the outer profile of the crown 21.

As illustrated in FIG. 4, the ring 1 forms a housing for the means for generating ultrasonic waves 2:
the truncated cone 11 extends under the crown 21, facing the first base 211, and
the skirt 12 encloses the crown 21.

Preferably, the height (i.e. dimension along the A-A' axis) of the ring-shaped wall 123 is greater than the height of the crown 21 so that the second ending 122 is localized at a non-zero distance from the second base 212.

This gives the possibility of defining a sufficient space above the crown 21 so that it is totally immersed once the probe is filled with a coupling fluid.

1.3. Means for Generating a Depression

The probe may include means for generating a depression allowing the maintaining in position of the ring 1 on the eye 4 during the whole period of the treatment.

The means for generating a depression for example comprise two suction nozzles 113 extending along a diameter of the second end 112.

Each nozzle 113 is connected to an external suction device (not shown) for generating a depression at the nozzles 113 when the probe is positioned on the eye 4. This gives the possibility of securing the ring 1 on the eye 4 by suction cup effect.

In an embodiment, each nozzle 113 consists in an aperture opening onto the second end 112 so as to come into contact with the eye 4 of the patient. This gives the possibility of limiting the risks of a pressure drop of the suction (notably relatively to a nozzle with an oblong shape).

Preferably, the nozzles 113 are laid out so as to be localized in the temporal/nasal plane B-B' of the eye 4 when the probe is applied on the eye 4. This gives the possibility of improving the efficiency of the suction cup effect of the ring 1 on the eye 4.

Indeed, the eye 4 has a substantially elliptical shape with a major radius contained in the temporal/nasal plane B-B'. By laying out the nozzles 113 so that they extend in the temporal/nasal plane B-B' when the probe is set into place, an intimate contact is ensured between the nozzles 113 and the eye 4, which improves the efficiency of the suction cup effect.

The means for generating a depression also comprise:
a ring-shaped conduit for circulation of air, and
a tubular access member 124
allowing the connection of the nozzles 113 to the external suction device via a connection tubing.

The ring-shaped conduit for circulation of air extends at the periphery of the second end 112. It allows the distribution of the depression generated at the nozzles 113.

The access member 124 extends radially towards the outside of the ring-shaped wall 123. Preferably, le access member 124 is laid out so as to be positioned in the temporal/nasal plane B-B' of the eye 4 when the probe is set into place on the eye 4. This gives the possibility of not bothering the practitioner with the connection tubing during the treatment.

1.4. Filter

As indicated earlier, the acoustic resistance of the air is very significant, the presence of an air bubble at a transducer 215 makes the latter inefficient. These air bubbles may be produced during the filling of the probe with the coupling fluid.

Within the scope of the present invention, this filling is applied by projecting the coupling fluid on the second base 212 of the crown 21 after having assembled the ring 1 with the means for generating ultrasonic waves 2.

In order to avoid the risks of accumulation of air bubbles between the transducers 215 and the eye 4, the probe comprises a flow rate regulator between the first and second_bases. The latter gives the possibility of preventing the circulation of air bubbles towards the first base 211.

In this embodiment illustrated in FIG. 4, the flow regulator comprises a conduit for supplying a coupling fluid. This conduit for example consists in an aperture 3 between the ring-shaped wall 123 and the external side wall 213. The dimensions of this aperture 3 are provided so as to retain the bubbles on the second base 212.

This aperture also allows the passing of the coupling fluid poured on the second base 212 towards the truncated cone 11. Advantageously, at least one of the dimensions of the aperture (and notably its thickness) is calculated so as to limit the propagation of bubbles towards the first base when the coupling fluid has a viscosity equal to that of water.

Thus, it is guaranteed that the retention function of the bubbles (on the second base) is fulfilled by the flow rate regulator with any type of coupling fluid which is more viscous than water.

Preferably, the distance between the skirt 12 and the crown 21 is constant in order to define a ring-shaped aperture 3 between the skirt 12 and the crown 21.

The distance between the skirt 12 and the crown 21 may be comprised between 0.1 and 5 millimeters, preferentially between 0.5 and 2 millimeters. This allows the aperture 3 to filter the bubbles with a diameter greater than its thickness (i.e. dimension of the aperture according to a radius of the truncated cone) while guaranteeing sufficient cooperation between the ring 1 and the means for generating ultrasonic waves 2.

Splines may be made in the annular wall 123 and/or in the external side wall 213 for facilitating the flow of the coupling fluid towards the truncated cone 11 during the filling of the probe. This gives the possibility of increasing the flow rate of the coupling fluid in order to avoid risks of overflow during the filling. The splines may extend over the whole or part of the height (i.e. the dimension along the A-A' axis) of the crown 21.

Even if the flow rate regulator allows retention of the majority of the bubbles contained in the coupling fluid during the filling, micro-bubbles may nevertheless circulate in the fluid flow flowing between the second and first bases 212, 211.

This is why the surface of the crown 21 may be treated for increasing its hydrophilic properties. For example, the transducer(s) may be covered with a layer of hydrophilic material. This gives the possibility of limiting the adhesion of air bubbles on the transducer(s) 215.

1.5. Purger

The probe also comprises a purger for discharging the air contained in the ring 1 during the filling of the probe.

The purger includes a chimney 218 coaxial with the central channel. This chimney 218 extends at right angles from the internal side wall 214.

The chimney 218 gives the possibility of preventing the flow of the coupling fluid through the central channel during the filling of the probe. Thus, it forces the fluid to flow through the aperture 3 forming a flow rate regulator.

Advantageously, the free end of the chimney 218 comprises a hole for allowing the air to escape. Indeed, during the filling of the probe, the coupling fluid gradually takes the place of the air contained in the ring 1. The air tends to accumulate in the central channel of the crown 21. The hole made in the chimney then allows this air to escape outwards from the probe.

1.6. Gripping Means

The probe also comprises gripping means for facilitating its handling by the practitioner, and giving him/her an indication on the area where his/her fingers are positioned.

Preferably, the gripping means include:
a first gripper positioned on the skirt 12 for allowing the practitioner to hold the ring 1 between his/her thumb and his/her forefinger, and a second gripper positioned on the crown 21 for allowing the practitioner to handle the means for generating ultrasonic waves 2 between his/her finger and his/her forefinger.

The first gripper for example consists in two pins 125 extending radially towards the outside of the ring-shaped wall 123. Advantageously, the pins 125 may be laid out on the ring-shaped wall 123 so as to be positioned in an upper/lower plane C-C' (orthogonal to the temporal/nasal plane B-B') when the probe is set into place on the eye 4. This allows the practitioner to be in an ergonomic position and be always placed at the head of the patient.

In order to improve the gripping of the ring 1, each pin 126 may have a concave possibly striated surface. This gives the possibility of reducing the risk of an accidental sliding between the first gripper and the surgical glove of the practitioner (which may in certain cases be humid).

The second gripper may consist in free ends of two tabs 219 elastic and planar with shape memory. As illustrated in FIG. 4, these two tabs 219 are positioned facing each other along a diameter of the crown 21, and extend and protrude at the periphery of the second base 212, in the extension of the external side wall 213.

A preformed dug imprint may be made at the end of each tab 219 in order to limit the risks of sliding of the surgical glove of the practitioner on the second gripper.

1.7. Guide in Translation

The probe also comprises a guide in translation for facilitating the assembly of the means for generating ultrasonic waves with the ring 1.

This gives the possibility of guaranteeing an accurate and repeatable positioning of the means for generating ultrasonic waves 2 relatively to the ring 11.

In the embodiment illustrated in FIG. 1, the guide in translation consists in:
  a groove 126 laid out on the ring 1 and
  a slider 216 laid out on the means for generating ultrasonic waves 2.

The groove 126 is made on the inner face of the ring-shaped wall 123. This groove 126 is adapted for receiving the slider 216.

The slider 216 radially extends towards the outside of the external side wall 213. The slider 216 may consist in a finger extending over one portion or over the totality of the height of the crown 21.

The guide in translation gives the possibility of preventing the relative rotation of the means for generating ultrasonic waves 2 relatively to the ring 1 around the axis A-A'.

The use of a slider 216 intended to cooperate with a groove 126 gives the possibility of giving the practitioner an indication on the orientation of the means for generating ultrasonic waves 2 relatively to the ring 1, the means for generating ultrasonic waves 2 not being only able to penetrate into the ring 1 along a single orientation.

1.8. Blocker in Translation

The probe may also comprise a blocker for attaching reversibly the means for generating ultrasonic waves 2 on the ring 1.

The blocker gives the possibility of immobilizing (in translation) the means for generating ultrasonic waves 2 once the probe is assembled. It comprises:
  two bulges 230 on the means for generating ultrasonic waves 2,
  two bulges 130 on the ring 1.

Each bulge 230 is mounted on a respective elastic tab 219 and extends while radially protruding outwards on the whole width of the tab 219.

Each bulge 230 is intended to cooperate with a respective bulge 130 made on the second ending 122 and radially extending inwards (i.e. in the direction of the A-A' axis).

1.9. Down Holder

In order to limit the mechanical plays between the ring 1 and the means for generating ultrasonic waves 2, the probe may also comprise a down holder for applying a down holding force on the means for generating ultrasonic waves 2.

Advantageously, a component of this down holding force is parallel to the axis A-A' and oriented towards the truncated cone 11 so as to flatten the ring 21 against the supporting cradle of the truncated cone 11.

In the embodiment illustrated in FIGS. 1 to 4, a down holder is laid out on each bulge 230. This down holder consists in an angle formed between a normal to the tab and the surface of the bulge 230 intended to come into contact with its associated bulge 130.

1.10. Abutment

The probe may also comprise a pair of associated abutments each to a respective tab 219. These abutments have the function of limiting the travel of the tabs 219.

This gives the possibility of reducing the risks of deterioration of the tabs 219 by applying a too large clamping force during the grasping of the means for generating ultrasonic waves 2.

In the embodiment illustrated in FIG. 4, each abutment consists in a rigid blade 231 extending parallel to its associated tab 219. The application of a clamping force on the tabs 219 induces their torsion towards the axis A-A' until a limiting position where the tabs 219 will come into contact with the blades 231. Beyond this limiting position, the displacement of the tabs 219 towards the axis A-A' is prevented by the blades 231.

In order to increase the rigidity of the blades 231, each abutment may comprise a buttress 232.

2. Use of the Probe

An example of the procedure for using the probe for treating the eye of a patient lying down on an operating table will now be described.

In a step of the procedure, the ring 1 and the means for generating ultrasonic waves 2 are connected to a control system. More specifically:
  the ring 1 is connected to a suction device of the control system by means of a connection tubing,
  the means for generating ultrasonic waves 2 are connected to a generator of the control system by means of an electric cable.

In another step, the practitioner grips the ring 1 by grasping the pins 125 between his/her thumb and his/her forefinger. He/she positions himself/herself at the front of the patient and lays the ring 1 on the eye 4 by putting the second end 112 in contact with the eye 4.

The suction device is activated for generating a depression at the nozzles 113 so as to secure the ring 1 on the eye 4 by a suction effect.

If need be, and before activating the depression, the practitioner displaces the ring 1 for centering it on the eye 4.

Once the ring 1 is centered on the eye 4, the practitioner takes the means for generating ultrasonic waves 2 by clamping the ends of the elastic tabs 219 between his/her thumb and his/her forefinger. He/she positions the crown 21 above the skirt 12.

The practitioner then aligns the slider 216 with the groove 126 by rotating the crown 21 around the axis A-A'. Once the slider 216 and the groove 126 are aligned, the practitioner slides the crown 21 inside the ring 1 so that the ring-shaped wall 123 surrounds the external side wall 213.

During the relative displacement of the crown 21 relatively to the ring 1, the bulges 230 will come into contact with the bulges 130. The elastic tabs 219 deform until the bulges 230 have crossed the bulge 130, and then reassume their rest positions.

The crown 21 is then blocked in the ring 1 by clipping by means of the bulges 230 and bulges 130. The V shape of the bulges 230 induces the constant application of a force against the bulges 130 which tend to flatten the crown 21 against the cradle of the truncated cone 11 in order to ensure accurate positioning of the means for generating ultrasonic waves 2.

Once the probe is assembled, the latter is filled with the coupling liquid. The practitioner positions the flask drop wise above the probe and pours the liquid onto the second base 212.

The liquid spreads over the second base 212 and flows through the aperture 3 for filling the ring 1. The chimney 218 prevents the liquid from penetrating into the central channel. The air bubbles with a diameter greater than the width of the aperture 3 (i.e. dimension of the aperture along a radius of the crown) are retained at the second base 212.

Gradually during the filling of the ring 1, the liquid gradually takes the place of the air which escapes through the hole of the chimney 218 via the central channel extending as far as the center of the first concave base 211.

When the crown 21 is totally immersed, the practitioner interrupts the filling and activates the control device for applying the treatment.

By limiting the risks of the presence of an air bubble at a transducer, the probe described earlier guarantees to the practitioner good efficiency of the treatment.

The reader will have understood that many modifications may be provided to the invention described earlier without materially departing from the new teachings and advantages described here. Therefore, all the modifications of this type are intended to be incorporated inside the scope of the appended claims.

The invention claimed is:

1. A probe for treating an eye pathology comprising:
    a ring including a truncated cone and a skirt coaxial with the truncated cone, wherein the truncated cone has a first end which supports means for generating ultrasonic waves and a second end which comes into contact with an eye of a patient, and
    the means for generating ultrasonic waves including a crown, wherein the crown has a first base facing the first end and a second base opposed to the first base, the skirt extending outwards from the first end and surrounding the crown,
    a guide configured to guide sliding of the means for generating ultrasonic waves relatively to the ring, and
    a flow rate regulator comprising an aperture defined between the skirt and the crown, the first base of the crown is configured to be releasably coupled with the first end of the ring in order to define the aperture, wherein thickness of the aperture is in a range between 0.1 mm and 5 mm, and wherein said aperture extends over a whole height of the crown so that the flow rate regulator is configured to:
    allow passing of a coupling fluid between the second and first bases, said coupling fluid allowing transmission of ultrasonic waves towards the eye of the patient, and
    eliminate bubbles contained in the coupling fluid flowing towards the first base during filling of the probe with said coupling fluid.

2. The probe according to claim 1, wherein the aperture extends over a whole perimeter of the crown.

3. The probe according to claim 1, wherein the first base of the means for generating ultrasonic waves comprises a hydrophilic treatment.

4. The probe according to claim 1, further comprising a purger for an exhaust of gases during the filling of the probe with the coupling fluid.

5. The probe according to claim 4, wherein the crown having a central channel, and the purger comprising at least one chimney coaxial with the central channel and extending outwards on the second base.

6. The probe according to claim 1, wherein the guide includes a groove laid out on the ring and a slider laid out on the means for generating ultrasonic waves.

7. The probe according to claim 1, further comprising at least two suction nozzles on the second end, the at least two suction nozzles being laid out so as to be localized in a transversal plane of the eye when the probe is positioned on the eye.

8. The probe according to claim 1, wherein the means for generating ultrasonic waves comprise a gripper extending on the second base.

9. The probe according to claim 1, further comprising blockers for immobilizing the ring relatively to the means for generating ultrasonic waves.

10. The probe according to claim 9, wherein the blockers comprise a pair of elastic tabs with shape memory extending at a periphery of the second base, each tab including a bulge for cooperating by clipping with a bulge made on the ring so as to immobilize in translation the ring relative to the means for generating ultrasonic waves.

11. The probe according to claim 10, wherein each bulge has a V-shape.

12. The probe according to claim 10, further comprising at least one abutment for limiting displacement of the pair of elastic tabs.

13. The probe according to claim 1, wherein a thickness of the aperture is between 0.2 and 2 mm.

14. The probe according to claim 1, wherein a thickness of the aperture is equal to 0.5 mm.

* * * * *